United States Patent [19]

Craig et al.

[11] Patent Number: 4,703,018

[45] Date of Patent: Oct. 27, 1987

[54] HIGH REFRACTIVE INDEX HALOALKYL-FUNCTIONAL SHELL-CORE POLYMERS AND THEIR USE IN LIGHT SCATTERING IMMUNOASSAYS

[75] Inventors: Alan R. Craig; Eileen G. Gorman, both of Wilmington, Del.

[73] Assignee: E. I. Du Pont de Nemours and Company, Wilmington, Del.

[21] Appl. No.: 703,424

[22] Filed: Feb. 20, 1985

[51] Int. Cl.[4] .......................................... G01N 33/543
[52] U.S. Cl. .................................... 436/518; 436/528; 436/531; 436/532; 436/533; 436/534; 436/823; 436/805
[58] Field of Search ............... 436/518, 528, 531, 532, 436/533, 534, 823, 805

[56] References Cited

U.S. PATENT DOCUMENTS

| | | | |
|---|---|---|---|
| 4,017,442 | 4/1977 | Gibbs et al. | 260/29.6 |
| 4,056,501 | 11/1977 | Gibbs et al. | 260/29.6 |
| 4,059,685 | 11/1977 | Johnson | 436/533 |
| 4,064,080 | 12/1977 | Daniel | 260/3 |
| 4,080,264 | 3/1978 | Cohen et al. | 436/514 |
| 4,181,636 | 1/1980 | Fischer | 260/8 |
| 4,401,765 | 8/1983 | Craig et al. | 436/533 |
| 4,480,042 | 10/1984 | Craig et al. | 436/533 |

OTHER PUBLICATIONS

Litchfield et al, Clin. Chem., vol. 30(9) 1984, 1489–93.
*Data Sheet No.* 238, 1983, Polysciences, Inc., Warrington, PA.

*Primary Examiner*—Christine M. Nucker
*Attorney, Agent, or Firm*—George A. Frank

[57] ABSTRACT

Novel particle reagent for light scattering immunoassays are provided. The particle reagents are high refractive index shell-core polymers, having at least a partial surface coverage by a monomolecular layer of anionic surfactant, covalently bonded to compounds of biological interest. The novel particle reagents are particularly suited to protein immobilization by covalent bonding to the shell and are especially useful for light scattering immunoassays.

10 Claims, No Drawings

HIGH REFRACTIVE INDEX HALOALKYL-FUNCTIONAL SHELL-CORE POLYMERS AND THEIR USE IN LIGHT SCATTERING IMMUNOASSAYS

TECHNICAL FIELD

This invention relates to novel particle reagents based on shell-core particles in which the high refractive index of the core results in high sensitivity light scattering measurements and the shell contains a polymer of chloromethylstyrene.

BACKGROUND ART

Agglutination reactions are known to produce aggregates that can be visually or instrumentally detected for qualitative or quantitative assay of biological materials. Agglutination reactions for antigens usually involve antibodies or other binding agents having at least two combining sites specific for multiple, complementary sites on their corresponding antigens or binding partners. These antigens can be found associated with bacterial and mammalian cell surfaces, viral capsids and envelopes, and as soluble and insoluble materials of biological interest such as proteins, carbohydrates, and nucleic acids. Alternatively, agglutination assays for antibodies having a minimum of two antigen-reactive sites are accomplished by adding the multivalent antigen to a solution containing the antibodies. Also useful are agglutination inhibition assays in which a known quantity of labelled, multiepitopic antigen or multivalent antibody competes with an unknown quantity of antigen or antibody, respectively, for combining sites on the binding partner, thereby reducing the extent of agglutination.

The extent of agglutination reactions is known to depend upon the relative concentrations of binding partners. Optimal concentration ranges for each can be empirically determined to provide conditions under which extensive cross-linking of reactants occurs. This cross-linking of individual binding partners provides efficient light scattering aggregates, which can be visually or spectrophotometrically detected. A molar excess of either binding partner relative to the other diminishes or eliminates the cross-linking agglutination reaction in a phenomenon known as the prozone effect, which reduces assay sensitivity. Therefore, maximum assay sensitivity is assured by adjustment of binding partner concentrations into optimal ranges as determined by maximal changes in the light scattering properties of an agglutination or agglutination inhibition reaction.

Sensitivity enhancement has been achieved in agglutination-based immunoassays by attaching immunoreagents to particulates whose improved light scattering efficiency provides additional changes in light scattering signal for each agglutination event. Immunoreagents have been adsorbed onto particulate materials such as latex shperes, or covalently bonded to specific functional groups on particle surfaces for improved stability. U.S. Pat. No. 4,064,080, issued Dec. 20, 1977, discloses styrene polymers with terminal aminophenyl groups having proteins attached to them. U.S. Pat. No. 4,181,636, issued Jan. 1, 1980, discloses carboxylated latex polymers coupled to immunologically active materials through a water soluble activating agent and their use as diagnostic reagents in agglutination tests.

Improved latex reagents are disclosed in U.S. Pat. No. 4,401,765, issued Aug. 30, 1983, comprising shell-core latex polymer particles of 0.03–0.1 $\mu$m diameters having a high refractive index polymer core and a polymer shell containing reactive groups such as epoxy, carboxyl, amino, hydroxyl, or formyl groups for covalent coupling of proteins. These improved latexes provide a high refractive index core which maximizes light scattering efficiency while also providing selected functional groups for hapten and protein immobilization onto reactive shells.

Core-shell latex particles of 0.05–1.0 $\mu$m diameters having active halogen monomers copolymerized with other ethylenically unsaturated monomers in the particle shell are disclosed in U.S. Pat. No. 4,017,442, issued Apr. 12, 1977. These particles are characterized by having cationic or nonionic surfaces generated by use of surfactants during or after particle polymerizations. Microparticles comprising monodisperse latex beads of 0.5 $\mu$m mean diameter and containing copolymerized chloromethylstyrene are commercially available from Polysciences, Inc., Warrington, PA., 18976, for use with covalently bound antigens and antibodies in agglutination tests. These particles are made from styrene copolymerized with chloromethylstyrene and cross-linked with divinylbenzene. U.S. Pat. No. 4,056,501, issued Nov. 1, 1977, discloses further treatment of the particle reagents prepared according to U.S. Pat. No. 4,017,442, previously cited, with nucleophilic groups such as dialkylsulfides or quaternary amines to react with the halogenated latexes to form stable, dispersed particle suspensions in aqueous media. These suspensions were shown to be useful for coatings and organic pigments.

Many of the functional groups found on particle reagents of the prior art are often less than optimal for protein immobilization. For example, some polymeric latex particles having functional groups such as carboxyl and amino groups, require activation prior to protein coupling. The outcome of such a process is variable with respect to the degree of activation and the stability of proteins once they are attached. In other cases such as with epoxy groups, activation is not required, but the active functional groups on the particles are hydrolytically unstable. This results in variably reactive particles that can provide a low concentration of covalently attached proteins. Finally, with functional groups which are either themselves reactive (autoreactive) or require an activation process, the protein coupling conditions may be too stringent requiring the use of elevated temperatures over long periods in the presence of surfactants to effect covalent protein attachment to particles. Such conditions can result in protein denaturations, which can be tolerated only if antigenic identity is sufficiently maintained to allow recognition by complementary binding partners, such as antibodies. However, immobilization of functional proteins such as enzymes, antibodies, specific binding proteins, etc. must be performed in a benign manner in order to preserve their binding or reactive properties.

There is a need for high refractive index particle reagents for use in specific binding assays, especially immunoassays, that provide reactive groups for covalent protein attachment under mild conditions that preserve protein functional or antigenic integrity. This is especially critical when proteins of interest are scarce or have multiple subunits with active binding regions which might be rendered less active by disassociation under severe coupling conditions. Having autoreactive functional groups capable of coupling to proteins under mild conditions and which remain stable and active upon storage in aqueous media and in the presence of other reagents such as detergents and salts, would minimize reagent manipulations and maximize product reproducibility from separate syntheses. A core-shell particle having stable, autoreactive shell functional groups that covalently immobilize proteins under mild coupling conditions, would be highly desireable to provide useful reagents for light scattering specific binding assays.

DISCLOSURE OF THE INVENTION

The particle reagent of this invention has a high refractive index and consists essentially of:

A. a polymer particle having an inner core and an outer shell wherein the inner core is a polymer having a refractive index of not less than 1.54 as measured at the wavelength of the sodium D line and wherein the outer shell is a polymer of
(1) at least five parts by weight of the outer shell of an ethylenically unsaturated monomer having a haloalkyl functional group capable of reacting with a compound of biological interest, its antigen or its antibody, selected from the group consisting of

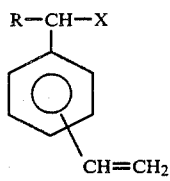

wherein X is Cl or Br and R is H, CH$_3$, or C$_2$H$_5$,
(2) optionally other ethylenically unsaturated monomers in amounts not resulting in the formation of water soluble polymer particles, and
(3) not more than 10 parts by weight of the outer shell of the residual monomers of the inner core;
said outer shell being formed by polymerization in the presence of said inner core; and wherein said polymer particle has an approximate diameter range of 0.01–1.0 μm, a 5–100% surface coverage by a monomolecular layer of anionic surfactant, and is covalently attached to B. a compound of biologicl interest, its antigen or its antibody.

The method of this invention for the detection and measurement of compounds of biological interest (which are intended to include the analogs of such compounds), their antibodies or antigens utilizes the particle reagents as described above.

DESCRIPTION OF THE INVENTION

This invention relates to novel particle reagents having high immunoreactivity and which are useful in high sensitivity light scattering immunoassays. These particle reagents are an improvement over the core-shell particles disclosed in commonly assigned U.S. Pat. No. 4,401,765, issued Aug. 30, 1983, incorporated herein by reference, in that they provide reactive halide groups on the surface of core-shell particles that impart several advantages.

The activated shell monomers having halide leaving groups such as chloride and bromide are reactive with protein amine and amide groups. There is no requirement for a separate, preliminary activating step to render the particle reagents reactive with desired biological materials. This convenience allows fewer handling and transfer steps in the preparation of particle reagents. In addition, the halide leaving groups on the particle shell are sufficiently stable to hydrolysis under various conditions of pH, ionic strength, temperature, etc. during aqueous storage and handling that a significant proportion of the reactive groups are retained. This reactive group stability provides greater control over covalent immobilization of materials of biological interest. For purposes of brevity, materials of biological interest include their antigens and antibodies. Further, the hydrolytic stability of the halide groups under particle synthetic conditions allows the preparation of well defined reagents having a known proportion of reactive groups. For example, a chloromethylstyrene monomer can be polymerized onto a polymer core in any proportion to other halide or non-halide containing monomers, to produce a shell having from 5 to 100% chloromethylstyrene monomers. The original proportion of reactive groups can be maintained in an aqueous environment for a sufficient period to allow the reproducible synthesis of core-shell polymer particles that can be later reacted with proteins in a reproducible manner.

Shell compositions that comprise from about 10 to 100% haloalkyl monomers are generally more useful and preferred in making the particle reagents of this invention. Shell compositions comprising less than 10% haloalkyl monomers and other ethylenically unsaturated monomers, while capable of immobilizing biological materials, do so in amounts too low to be useful. Immunoassays performed using particle reagents having shell compositions with less than 10% haloalkyl monomers are expected to be less sensitive than those using particle reagents derived from shell compositions having greater than 10% haloalkyl monomer. However, in those assay circumstances where a reduced level of immobilized biological material may be desired such as to encourage cross-linking even where only low levels of divalent antibody are available, the particle reagents having shells with less than 10% but at least 5% haloalkyl monomers may be useful.

The advantages of the core-shell particle configuration disclosed in U.S. Pat. No. 4,401,765 are maintained in the present invention. The light scattering properties of particle suspensiions depend on several variables, most importantly the particle size, the refractive indices of the core and the suspension medium, and the wavelength of light used for measurement. Thus, the selection of core material, particle size, and wave-length of detection of the agglutination reaction are all important factors in optimizing assay sensitivity. These factors can be determined by the type of light scattering detection means used.

During visual observation of the agglutination reaction, a broad band of wavelengths, between approximately 400 and 600 nm, can be utilized. Since the light scattering response varies over this wavelength range, the visual observation results in an averaging of the effects of many wavelengths which is less sensitive than choosing the optimum wavelength for a given particle size and refractive index. For particles whih are small compared to the wavelength of light, the scattering increases with the inverse 4th power of the wavelength and the magnitude is dependent upon the refractive index, when the wavelength of light approaches an adsorption band of the particle, there is an increase of refractive index and thus the light scattering properties are sensitive also to the optical dispersion of the scattering element and the wavelength functionality may exceed the 4th power.

For the turbidimetric detection of particle size change at a given wavelength or measurement it is imperative that the particle size and refractive index be chosen with care since the turbidimetric signal goes through a maximum, producing a double-valued response with little or no sensitivity at the peak. In addition, the slope sensitivity is greater on the small particle size side of the peak than on the large and it increases with increasing refractive index ratio of particle to medium.

For these reasons, small particles of high refractive index with short wavelength detection are preferred for high sensitivity. There is a practical limit in the ultraviolet region for measurement of samples in serum because of light adsorption by proteins and other components. Thus, convenient wavelengths are those in excess of approximately 320 nm. Shorter wavelengths, such as 340 nm, give larger signal differences than longer wavelengths, such as 400 nm. In general, particle size range of 0.01-1.0 μm can be utilized in the particle reagent of this invention.

For nephelometric detection, the optimum sensitivity can depend not only on particle size and wavelength, but also on the angle of measurement. Nephelometry refers to the measurement of the light scattered at an angle from the incident beam. The size of the particles for optimum sensitivity will have an angular dependence as well as a wavelength dependence.

Other types of scattering measurements of the agglutination reaction include particle counting, quasi-elastic light scattering, autocorrelation spectroscopy, and measurements of the dissymmetry or the polarization of the particles. These types of measurements provide different constraints for the particle reagents.

In all types of measurements, however, the higher the refractive index of the particles at the wavelength of choice, the higher the light scattering signal.

A preferred way of measurement of immunological reactions utilizing the particle reagents of this invention is by turbidity since no special equipment is required other than a spectrophotometer which is generally available in clinical laboratories. The spectrophotometer measures increased absorbance which is due to the increasing particle size resulting from the agglutination reaction. This increased absorbance is a direct measure of the agglutination caused by the analyte or an indirect measure of the agglutination inhibition caused by the analyte. To optimize the turbidity change which occurs during agglutination, it is important to select the particle size with care.

During the agglutination reaction, the effective particle size increases. For sensitive measurements it is, therefore, important to choose the wavelength at which the signal change for a given particle size change is optimal.

Because of the importance of the refractive index for turbidimetric detection of the agglutination reaction, core materials are restricted to those which will produce acceptable signal changes for the desired assay sensitivity. For analytes in high concentrations (μg/mL range), the choice is not critical, but for analytes in the nanogram/mL range, particles having high refractive index are necessary. Thus, core polymers with high aromaticity and high atomic weight substituents are preferred over aliphatic polymers and, in general, polymers of high refractive indices are preferred over polymers with lower refractive indices.

The inner core of the polymer particles can be selected from a large group of materials with high refractive index. Preferred are those materials which can be prepared by emulsion polymerization in a manner so that the final particle size is controllable and is substantially uniform. Polymers utilized in the inner core of the polymer particles have refractive indices greater than 1.54 (at the Na D line; 569 nm) and are listed in Table 1. Since the refractive index is a function of wavelength, the scattering properties will be dependent upon the wavelength of measurement. In general, the refractive index is greater at shorter wavelengths.

TABLE 1

REFRACTIVE INDICES OF POLYMERS

| Polymer | $n_D$ |
|---|---|
| Cellulose | 1.54 |
| Poly(vinyl chloride) | 1.54–1.55 |
| Urea-formaldehyde resin | 1.54–1.56 |
| Poly(sec-butyl α-bromoacrylate) | 1.542 |
| Poly(cyclohexyl α-bromoacrylate) | 1.542 |
| Poly(2-bromoethyl methacrylate) | 1.5426 |
| Poly(dihydroabietic acid) | 1.544 |
| Poly(abietic acid) | 1.546 |
| Poly(ethylmercaptyl methacrylate) | 1.547 |
| Poly(N—allyl methacrylamide) | 1.5476 |
| Poly(1-phenylethyl methacrylate) | 1.5487 |
| Poly(vinylfuran) | 1.55 |
| Poly(2-vinyltetrahydrofuran) | 1.55 |
| Poly(vinyl chloride) + 40% tricresyl phosphate | 1.55 |
| Epoxy resins | 1.55–1.60 |
| Poly(p-methoxybenzyl methacrylate) | 1.552 |
| Poly(isopropyl methacrylate) | 1.552 |
| Poly(p-isopropylstyrene) | 1.554 |
| Poly(chloroprene) | 1.554–1.55 |
| Poly(oxyethylene)-α-benzoate-α-methacrylate) | 1.555 |
| Poly(p,p'-xylylenyl dimethacrylate) | 1.5559 |
| Poly(1-phenylallyl methacrylate) | 1.5573 |
| Poly(p-cyclohexylphenyl methacrylate) | 1.5575 |
| Poly(2-phenylethyl methacrylate) | 1.5592 |
| Poly(oxycarbonyloxy-1,4-phenylene-1-propyl-butylidene-1,4-phenylene) | 1.5602 |
| poly[1-(o-chlorophenyl)ethyl methacrylate] | 1.5624 |
| Poly(styrene-co-maleic anhydride) | 1.564 |
| Poly(1-phenylcyclohexyl methacrylate) | 1.5645 |
| Poly(oxycarboxyloxy-1,4-phenylene-1,3-dimethylbutylidene-1,4-phenylene) | 1.5671 |
| Poly(methyl α-bromoacrylate) | 1.5672 |
| Poly(benzyl methacrylate) | 1.5680 |
| Poly[2-(phenylsulfonyl)ethyl methacrylate] | 1.5682 |
| Poly(m-cresyl methacrylate) | 1.5683 |
| Poly(styrene-co-acrylonitrile) | 1.57 |
| (ca. 75/25) | 1.57 |
| Poly(oxycarbonyloxy-1,4-phenyleneisobutylidene-1,4-phenylene) | 1.5702 |
| Poly(o-methoxyphenyl methacrylate) | 1.5705 |
| Poly(phenyl methacrylate) | 1.5706 |
| Poly(o-cresyl methacrylate) | 1.5707 |
| Poly(diallyl phthalate) | 1.572 |
| Poly(2,3-dibromopropyl methacrylate) | 1.5739 |
| Poly(oxycarbonyloxy-1,4-phenylene-1-methylbutylidene-1,4-phenylene) | 1.5745 |
| Poly(oxy-2,6-dimethylphenylene) | 1.575 |
| Poly(oxyethyleneoxyterephthalate) | 1.575 |
| Poly(vinyl benzoate) | 1.5775 |

TABLE 1-continued

| REFRACTIVE INDICES OF POLYMERS | |
|---|---|
| Polymer | $n_D$ |
| Poly(oxycarbonyloxy-1,4-phenylene-butylidene-1,4-phenylene) | 1.5792 |
| Poly(1,2-diphenylethyl methacrylate) | 1.5816 |
| Poly(o-chlorobenzyl methacrylate) | 1.5823 |
| Poly(oxycarbonyloxy-1,4-phenylene-sec-butylidene-1,4-phenylene) | 1.5827 |
| Poly(oxypentaerythritoloxyphthalate) | 1.584 |
| Poly(m-nitrobenzyl methacrylate) | 1.5845 |
| Poly(oxycarbonyloxy-1,4-phenylene-isopropylidene-1,4-phenylene) | 1.5850 |
| Poly(N—2-phenylethyl methacrylamide) | 1.5857 |
| Poly(4-methoxy-2-methylstyrene) | 1.5868 |
| Poly(o-methylstyrene) | 1.5874 |
| Poly(styrene) | 1.59–1.592 |
| Poly(oxycarbonyloxy-1,4-phenylene-cyclohexylidene-1,4-phenylene) | 1.5900 |
| Poly(o-methoxystyrene) | 1.5932 |
| Poly(diphenylmethyl methacrylate) | 1.5933 |
| Poly(oxycarbonyloxy-1,4-phenylene-ethylidene-1,4-phenylene) | 1.5937 |
| Poly(p-bromophenyl methacrylate) | 1.5964 |
| Poly(N—benzyl methacrylamide) | 1.5965 |
| Poly(p-methoxystyrene) | 1.5967 |
| Hard rubber (32% S) | 1.6 |
| Poly(vinylidene chloride) | 1.60–1.63 |
| Poly(sulfides) | 1.6–1.7 |
| Poly(o-chlorodiphenylmethyl methacrylate) | 1.6040 |
| Poly[oxycarbonyloxy-1,4-(2,6-dichloro)phenylene-isopropylidene-1,4-(2,6-dichloro)phenylene)] | 1.6056 |
| Poly[oxycarbonyloxybis 1,4-(3,5-dichlorophenylene)] | 1.6056 |
| Poly(pentachlorophenyl methacrylate) | 1.608 |
| Poly(o-chlorostyrene) | 1.6098 |
| Poly(phenyl α-bromoacrylate) | 1.612 |
| Poly(p-divinylbenzene) | 1.6150 |
| Poly(N—vinylphthalimide) | 1.6200 |
| Poly(2,6-dichlorostyrene) | 1.6248 |
| Poly(α-naphthyl methacrylate) | 1.6298 |
| Poly(α-naphthyl carbinyl methacrylate) | 1.63 |
| Poly(sulfone) | 1.633 |
| Poly(2-vinylthiophene) | 1.6376 |
| Poly(α-naphthyl methacrylate) | 1.6410 |
| Poly(oxycarbonyloxy-1,4-phenylene-diphenylmethylene-1,4-phenylene) | 1.6539 |
| Poly(vinyl phenyl sulfide) | 1.6568 |
| Butylphenol-formaldehyde resin | 1.66 |
| Urea-thiourea-formaldehyde resin | 1.660 |
| Poly(vinylnaphthalene) | 1.6818 |
| Poly(vinylcarbazole) | 1.683 |
| Naphthalene-formaldehyde resin | 1.696 |
| Phenol-formaldehyde resin | 1.70 |
| Poly(pentabromophenyl methacrylate) | 1.71 |

Not all of the polymers listed above can be utilized as the inner core for the particle reagents of this invention since there are additional criteria to be applied to the selection of core monomer materials. Cellulose, for example, is not readily prepared as uniform particle size spheres. Condensation polymers are also not useful since the polymerization process does not lead to spherical particles of the type which can be obtained by emulsion polymerization. Some thermoplastic polymers such as poly(oxyethylene-oxyterephthalate) and some thermosetting resins of the urea-formaldehyde type are not suitable.

The monomers of interest are those which contain vinyl or allyl groups in addition to substituents such as halides, aromatic, heterocyclic, unsaturated or carbocyclic groups which impart high refractivity.

Polymer particles useful for the preparation of the particle reagents of this invention can be prepared preferentially by emulsion polymerization. Staged emulsion polymerization can lead to a core/shell polymer approximating the desired refractive index of not less than $n_D=1.54$. To obtain a polymer of desired refractive index, it is preferred that the shell polymer not exceed approximately 10 parts by weight of the polymer particle.

A convenient way to control particle size of the polymer particles is to first prepare a seed emulsion whose size can be controlled by the amount of surfactant used. After preparation of the seed emulsion, additional monomer and surfactants can be added at a controlled rate to increase the size of the particles in the seed emulsion.

It is preferable to carry the conversion of the core monomer(s) to substantial completion so that the shell polymer be a homopolymer or a copolymer of known composition rather than a copolymer of unknown composition. Conversions in excess of 98% can be attained by increasing the temperature of the core emulsion to approximately 98° C. at the end of the polymerization. To further reduce the probability of producing particles whose surface is a copolymer of unknown composition, the shell monomer can be added gradually rather than batchwise. In such a manner, the residual core monomer(s) can be consumed during the early stages of the shell polymer formation.

The attachment of the shell polymer to the core can be accomplished by graft polymerization of the functional monomer to the residual ethylenically unsaturated groups in the core polymer or the functional monomer can be polymerized around the core to produce a contiguous shell. Preferred monomers include chloromethylstyrene and bromomethylstyrene, the most preferred being chloromethylstyrene.

The outer shell of the polymer particle can be prepared from a range of haloalkyl monomers having functional groups capable of reacting with desired biological materials, especially proteins. The outer shell can be a homopolymer of haloalkyl monomers or copolymers of such haloalkyl monomers and other ethylenically unsaturated monomers in amounts not resulting in the formation of water soluble polymer particles. The selection of appropriate outer shell monomers will depend largely upon their intended use. However, the copolymer compositions which include active haloalkyl monomers and other ethylenically unsaturated monomers can be prepared by controlled synthetic procedures to produce particle reagents having defined amounts of shell reactive groups.

The relative amount of the reactive haloalkyl groups in the shell affects the activity of the covalently attached biological material in a manner not clearly understood. The biological reactivity (such as antibody binding, enzyme activity, etc.) of the material covalently bound to the particle shell exhibits an optimum, when evaluated by functional assays such as immunoassays, enzyme-substrate reactions, etc., that is related to the amount of active halide in the shell. Therefore, control of the polymerization reactions which produce the shell polymers is important to insure that the concentration of reactive halide groups in the shell be reproducible. This control can be achieved by sequential synthesis of core and shell polymers in a manner that insures essentially complete core polymerization prior to shell polymerization. The outer shell should not contain more than 10 parts, preferably not more than 5 parts, and even more preferably not more than 2 parts, by weight of the outer shell of the monomers of the inner core. These limitations on inner core monomers are meant to apply only to the residual monomers not polymerized during the preparation of the inner core. Regulation of polymerization times, temperatures, surfactant levels, monomer concentrations, etc. allows the synthetic control required to produce defined shell compositions on polymer cores that result in polymer particles useful in the present invention.

The amount of active haloalkyl monomer polymerized into the particle shell has been unexpectedly found to influence the biological activity of covalently bound proteins such as antibodies. Lower amounts of haloalkyl monomers in the range of 10 to 30% (w/w) relative to other ethylenically unsaturated, inactive monomers in the particle shell, have been found to provide better specific binding activity of particle reagents having antibody covalently bound to them than in antibody particle reagents having shells polymerized with greater than about 30% (w/w) haloalkyl monomer. In contrast, proteins such a antigens, protein carriers of haptens, peptide hormones, etc. can be covalently immobilized onto particle shells composed of as much as 100% chloromethylstyrene without significant loss of identity to complementary binding agents. These observations suggest that immobilization of biologically functional materials such as antibodies, enzymes, hormone receptors, etc. that rely upon appropriate stereochemical associations of subunits to provide active sites should be performed using particles with shells having lower relative concentrations of active haloalkyl monomer in the range of 10 to 30% (w/w).

A preferred way of carrying out the shell polymerization process is in the presence of anionic surfactants (such as sodium dodecyl sulfate, lithium dodecyl sulfate, GAFAC ® RE610, a mixture of octyl and nonylphenyl ethers of polyoxyethylene terminated with a phosphate group, etc., preferably sodium dodecyl sulfate). Alternatively, anionic surfactant can be added after this process to create and maintain a net negative charge on the shell surface. This charged environment provides for the adsorption of biological materials, especially proteins, onto the hydrophobic particle shell without creating deleterious conditions that would promote denaturation or other irreversible changes that could severely diminish structural integrity or biological activity. The anionic surfactant also provides conditions that favor maintaining monodisperse particle suspensions during particle synthesis as well as after protein adsorption and covalent attachment to reactive shell groups. It has been found that anionic surfactant are useful in a concentration range such that at least 5% of the latex surface is covered with a monomolecular layer of surfactant.

Attempts to use cationic or, surprisingly, even nonionic surfactants to prepare particle reagents having biological materials covalently attached to them resulted in aggregated or inactive particle reagents. These reagents were unsuited for use in immunoassays when antibody or proteinaceous antigens were covalently bound to particle surfaces in the presence of cationic surfactants because of poor light scattering efficiency of the aggregated particle reagent. Use of a nonionic surfactant, such as Triton X-100, in place of cationic surfactants, produced a suitably dispersed particle preparation. However, attempts to attach proteins covalently to the haloalkyl groups on the particle shell failed to produce particles with any significant activity. Although the particle reagent remained sufficiently dispersed in the liquid medium, no useful immunoassays could be carried out with the reagent. It appears, therefore, that the use of anionic surfactants is an unexpected requirement for the preparation and use of the particle reagents of the present invention.

The present invention is further concerned with an immunologically active, stable particle reagent for use in sensitive light scattering immunoassays for detecting and measuring compounds of biological interest. These assays are contemplated to be used to detect and measure a wide variety of substances in biological fluids and cell and tissue extracts for which an immunological counter reactant can be produced. The compounds of biological interest include serum and plasma proteins, salivary, urinary or milk proteins, drugs, vitamins, horomones, enzymes, antibodies, polysaccharides, bacteria, protozoa, fungi, viruses, cell and tissue antigens and other blood cell or blood fluid substances. Of special interest are those substances for which a quantitative determination is required for the assessment of disease state.

The amount of haloalkyl monomer to be incorporated into the shell portion of the particle reagent of this invention can be dictated by the type and amount of biological material to be immobilized. For example, to immobilize antibody, a polymer particle having a shell containing from about 10 to 30% (w/w) chloromethylstyrene can be mixed with the appropriate amount of an anionic surfactant, such as SDS. The amount of surfactant can be calculated from the known (precalculated) particle surface area and from known surfactant parameters [from Polymer Handbook, Brandrup and Immergent (eds.), J. Wiley & Sons, $2^{nd}$ Edition (1975) Section II, p. 485]. It is preferable to provide sufficient anionic surfactant to cover between 40 and 100% of the particle surface with a surfactant monolayer. Protein can be added in molar excess over active shell halides in the range of a 5:1 to 50:1 molar ratio. After mixing in a buffered solution to insure complete exposure of particle surface functional groups to proteins, the mixture is allowed to incubate over a period of from 0.5 to 10 hours, preferably 0.5 to 3 hours, at a temperature in the range of 25° to 40° C. When incubation is carried out at 4° C., it should be extended over several days to achieve adequate covalent attachment of protein to the particles. After sufficient time has elapsed to allow covalent attachment, a separation of particle reagent from the suspending buffered medium is effected, usually by centrifugation, although filtration, gravitational settling, etc. would suffice to allow the removal of unbound protein.

In the preparation of antigen particle reagent, several washings of the particle reagent are performed with buffered solution, usually containing anionic surfactant. For example, a glycine or phosphate buffer can be used containing a surfactant such as GAFAC ® RE610, in the range of from 0.1 to 0.5% (w/v). The washings are carried out by sequential suspensions and separations of the particle reagent and removal of supernatants. This washing process is repeated a sufficient number of times, usually three to five times, until the supernatant solution contains substantially no protein.

The particle reagent so produced can be tested for immunoreactivity by turbidimetric assay with the binding partner complementary to the partner covalently linked to the polymer particle. The particle reagents of this invention exhibit a high degree of immunoreactivity, indicating that immunoreactants have been covalently linked to shell-core polymer particles in the presence of anionic surfactants, in a manner sufficiently benign to preserve a significant proportion of their original activity.

In other instances, such as immobilization of an antibody on polymer particles, where the antibody serves as a specific binding agent for materials of biological interest such as C-Reactive Protein, anionic surfactant does not have to be incorporated in the wash buffers. It is preferred that the level of anionic surfactant used in the synthesis of the core-shell polymer particle, prior to protein attachment, be sufficient to provide a calculated particle surface coverage of between about 40 and 70%. It has been found that antibody particle reagents are more active when the anionic surfactant is introduced during the polymerization process, rather than being added during protein attachment or in the wash buffers. When this method is used to bind antibodies to the haloalkyl shell groups, it is believed that sufficient anionic surfactant is associated with the particle surface during protein attachment to provide optimal conditions for maintenance of the appropriate particle dispersion, without deleteriously affecting antibody activity.

Antibodies appropriate for use in the present invention can include antibodies capable of binding antigen or hapten, are selected from any class or subclass of antibody, and can be polyclonal or monoclonal. Fragments of antibodies, such as F(ab')$_2$, F(ab'), and F(ab), can also be used. When monovalent antibody is used, it should be immobilized onto polymer particles to function as an agglutinating agent or when it is the compound of biological interest.

Immunoassays utilizing the particle reagents of this invention can be designed in a variety of ways depending on the type of analyte and on the required sensitivity. For example, for analytes in relatively high concentrations such as certain serum proteins, appropriate antibody particle reagents can be used in direct particle enhanced turbidimetric immuno-precipitation techniques.

The inhibition immunoassay method of this invention also requires, in addition to a particle reagent, a bi- or multi-functional agent, hereinafter referred to to as an agglutinating agent, to cause the agglutination of the particle reagent. It is this agglutination which can be initiated by the compound of biological interest. The agglutinating agent can be an antibody to the compound of biological interest or another particle reagent based on a polymer particle, as described above, covalently attached to an antibody of the compound of biological interest. The agglutinating agent can also be a multivalent conjugate of the compound of biological interest and a protein. Such a conjugate may be utilized in situations where the particle reagent utilized in the method of this invention contains a covalently attached antibody of the compound of biological interest.

For the measurement of haptens such as drugs, several different assay configurations can be utilized. In one such configuration, antigenic particle reagents can be prepared by attaching a hapten-protein conjugate to the polymer particle. The inhibition of the reaction between these particle reagents and the appropriate antibodies by the hapten of biological interest is determined. The reaction can be performed by direct competition for the antibody between the particle reagent and the sample hapten or by sequential reaction of the hapten with antibody followed by addition of the particle reagent.

Another assay configuration for haptens can utilize antibody particle reagent wherein the agglutination of the antibody particle reagents with soluble multi-haptenic protein conjugates is inhibited by the analyte (hapten). Such an assay can also be performed in a competitive or sequential mode. In yet another assay, both antibody and multi-haptenic particle reagents can be present, of the same or differing sizes, and the inhibition reaction by haptens can be performed in a competitive or sequential mode.

The agglutination reaction, in general, can be accelerated by the presence of an agglutinating accelerator. Such an accelerator can be a polyethylene glycol or an anionic surfactant such as sodium dodecyl sulfate.

The following examples are illustrative of the invention.

EXAMPLES

Example 1

Comparison of Particles Having Polychloromethylstyrene (PCMS) Shell and Particles Having Polyglycidyl Methacrylate (PGMA) Shell for Immobilization of Fibrinogen Degradation Products (FDP)

(A) Preparation of Polystyrene/Polyvinylnaphthalene/Polychloromethylstyrene Core-Shell Polymer Particles (i) Polystyrene Seed Emulsion Polymerization A polystyrene seed emulsion was prepared at room temperature (20° C.) by adding to a 4 L-Ehrlenmeyer flask, under a nitrogen atmosphere, 2.5 L deionized water, 400 g Dupanol WAQE (30% solution of SDS, available from E. I. du Pont de Nemours and Co.), 50 mL styrene, 20 g sodium metabisulfite, 200 mL of a 350 mg/mL potassium persulfate solution, and 125 mL of a ferrous sulfate solution (0.6 g of ferrous sulfate heptahydrate and 0.25 g of sulfuric acid dissolved in 500 mL of nitrogen-purged, deionized water). After 10 minutes, 25 g of Aerosol OT-100 dissolved in 376 mL of styrene was added at a rate of 30 mL/min. The mixture was stirred overnight. A sample of the product, diluted 1:100, had an optical density of 0.171 when measured at 340 nm.

(ii) 2-Vinylnaphthalene Core Polymerization

Latex polymerization to prepare polyvinylnaphthalene was carried out in a 250-mL round-bottomed flask equipped with a magnetic stirrer and a reflux condenser. 1.8 mL of the polystrene seed emulsion prepared in Example 1Ai above was added to 98 mL of water, and the mixture was heated to 95° C. This mixture was then added to 11.7 g of 2-vinylnaphthalene (2-VN, purified by sublimation and chromatography on basic alumina in a dichloromethane solution), 300 mg of sodium bicarbonate and 90 mg of potassium persulfate. As soon as the 2-vinylnaphthalene had melted, 4 mL of a 10% sodium dodecyl sulfate solution was added at a rate of 0.3 mL/min. One hour after the beginning of the SDS feed, the polymerization was conplete. The optical density of the product measured at 340 nm was 0.155 after diluting 1:5000 in water. The number average particle size was determined to be 0.074 μm by electron microscopy. The conversion of monomer to polymer was found to be 99.6% by gas chromatographic determination of the residual monomer.

(iii) Preparation of 2-VN/CMS Core-Shell Polymer 104 mL of the polyvinylnaphthalene latex prepared in Example 1Aii was preheated in the same apparatus as utilized above to about 95° C. and 100 mg of potassium persulfate and 2.06 mL of chloromethylstyrene (CMS, Polysciences Co.; mixed isomers) were added. After 1 hour, the mixture was cooled. The conversion of chloromethylstyrene to polymer was found to be 93% complete. The optical density of a 1:5000 diluted sample was measured at 340 nm and found to be 0.183.

(B) Preparation of Polyvinylnaphthalene/Polyglycidyl Methacrylate Core-Shell Polymer Particles (i) Polystyrene/polyvinylnaphthalene latex was prepared as in Example 1Aii.

(ii) Glycidylmethacrylate Shell Polymerization

The procedure used was the same as in Example 1Aiii, except that the polymerization time was 20 minutes, instead of 1 hour, and glycidyl methacrylate was substituted for chloromethylstyrene. The conversion of monomer to polymer was determined to be 99.0%. The final optical density of a 1:5000 diluted sample was 0.154 when measured at a wavelength of 340 nm.

(C) Immobilization of Fibrinogen Degradation Products (FDP)

1 mL of each final latex from Examples 1A and 1B in separate but identical procedures, was first mixed with a volume (specified below) of a 10% sodium dodecyl sulfate (SDS) solution and 4 mL of a 15 mM phosphate buffer, pH 7.5. This suspension was then added to a solution of 10 mg of FDP [prepared by the method of Matsushima et al., Thrombosis Research, Volume 27, 111–115 (1982)] in 5 mL of 15 mM phosphate buffer (as above). The pH of the mixture was adjusted to 7.8 using 0.1M sodium hydroxide, and incubated for the time and temperature indicated in Table 1.

After the specified incubation time, each latex was centrifuged at 20,000 RPM in a Sorvall® model RC-5B centrifuge (a registered trademark of E. I. du Pont de Nemours and Co.). The supernatant was decanted from the pellet of particles, and the pellet resuspended in a 0.1% solution of GAFAC® RE610 (an anionic detergent available from GAF Corporation) in 15 mM phosphate buffer, pH 7.5, by sonication for 3 minutes with a Heat Systems Ultrasonics model 225R sonicator. The suspension was again centrifuged and resuspended as above. Finally, it was centrifuged a third time, the supernatant decanted, and the particle pellet dried under vacuum.

The dried pellet was then analyzed for nitrogen content using the Kjeldahl method.

The results for the two types of latex are summarized below in Table 2.

TABLE 2

Covalent Attachment of FDP to Latex Particles

| Type of Shell | Volume of 10% SDS (μL) | Incubation Time (hour) | Incubation Temperature (°C.) | Nitrogen Content (%, Average) |
|---|---|---|---|---|
| PCMS | 100 | 0.5 | 4 | 0.005 |
|  | 100 | 0.5* | 4 | 0.385 |
|  | 100 | 24 | 4 | 0.175 |
|  | 100 | 24 | 37 | 0.335 |
| PGMA | 100 | 0.5 | 4 | 0.00 |
|  | 100 | 0.5* | 4 | 0.005 |
|  | 100 | 24 | 4 | 0.00 |
|  | 100 | 24 | 37 | 0.005 |
|  | 0 | 0.5 | 4 | 0.125 |
|  | 0 | 0.5* | 4 | 0.685 |
|  | 0 | 24 | 4 | 0.400 |

TABLE 2-continued

Covalent Attachment of FDP to Latex Particles

| Type of Shell | Volume of 10% SDS (μL) | Incubation Time (hour) | Incubation Temperature (°C.) | Nitrogen Content (%, Average) |
|---|---|---|---|---|
|  | 0 | 24 | 37 | 0.710 |

*Samples were centrifuged only once, then decanted, and the pellet dried and analyzed. From the data one can conclude that a single centrifugation results in incomplete removal of unbound FDP.

The data show that during polymer particle-protein interactions in the presence of SDS, even after two GAFAC® RE610 washings, FDP remains associated with the PCMS shell but not significantly associated with the PGMA shell. These results indicate that FDP is covalently linked to PCMS particles under the incubation conditions specified, but not to PGMA particles. (The covalent linkage of FDP with PCMS latex even at an incubation temperature of 4° C. was an added advantage since low temperatures are generally better suited to retention of biological activity of proteins than elevated temperatures.) In the absence of SDS, protein (FDP) did associate with PGMA but the particle reagent so produced was highly aggregated and was unsuitable for use in immunoassays for FDP.

The role played by the anionic surfactant in providing conditions to permit the production of useful PCMS-based particle reagents was surprising. In addition, the successful use of cationic and nonionic surfactants in association with a core-shell particle having haloalkyl functional groups (U.S. Pat. No. 4,017,442) provided no incentive to use anionic surfactants. In contrast, the failure to produce acceptable PGMA-based particle reagent in the presence of added anionic surfactant was also surprising in that U.S. Pat. No. 4,401,765 disclosed the use of anionic surfactants to produce particle reagents having protein covalently linked through the epoxy functional group of PGMA.

Example 2

Immobilization of Fibrinogen on Particles Having Polychloromethylstyrene Shell and Particles Having Polyglycidyl Methacrylate Shell The same procedures were used as in Example 1 except that fibrinogen, and not fibrinogen degradation products, was reacted with polymer particles at 4.9 mg/mL fibrinogen. Fifty percent higher SDS levels were also added during particle reagent synthesis. Fibrinogen was obtained from Helena Laboratories (Lot #8266781). The results are presented in Table 3.

TABLE 3

Covalent Attachment of Fibrinogen to Latex Particles

| Type of Shell | Volume of 10% SDS (μL) | Incubation Time (hour) | Incubation Temperature (°C.) | Nitrogen Content (%, Average) |
|---|---|---|---|---|
| PCMS | 150 | .5 | 4 | 0.305 |
|  | 150 | .5 | 4* | 0.505 |
|  | 150 | 24 | 4 | 0.420 |
|  | 150 | 24 | 37 | 0.370 |
| PGMA | 150 | .5 | 4 | 0.01 |
|  | 150 | .5 | 4* | 0.01 |
|  | 150 | 24 | 4 | 0.00 |
|  | 150 | 24 | 37 | 0.00 |
|  | 0 | .5 | 4 | ∞ |
|  | 0 | .5 | 4* | 1.35 |
|  | 0 | 24 | 4 | ∞ |

TABLE 3-continued

| | Covalent Attachment of Fibrinogen to Latex Particles | | | |
|---|---|---|---|---|
| Type of Shell | Volume of 10% SDS (μL) | Incubation Time (hour) | Incubation Temperature (°C.) | Nitrogen Content (%, Average) |
| | 0 | 24 | 37 | ∞ |

*Samples were centrifuged only once, then decanted, and the pellet dried and analyzed. From the data one can conclude that a single centrifugation results in incomplete removal of unbound fibrinogen.
∞ Particle pellets could not be resuspended after the first centrifugation The data show results similar to those obtained in Example 1. Fibrinogen is associated with PCMS in the presence of SDS at both 4° and 37° C., but not with PGMA latex. When no additional SDS was added during the procedure, the PGMA particle reagents were so highly aggregated after the first centrifugation that they could not be resuspended for further processing.

Example 3

Immobilization of Rabbit IgG Protein on Particles Having Polychloromethylstyrene Shell and Particles Having Polyglycidyl Methacrylate Shell Rabbit IgG (Cappel Diagnostics; chromatography purified Lot #20872) was attached to latex polymer particles, prepared in Examples 1A and 1B, using the same protocol as was used with FDP in Example 1. The data for comparison of immobilized protein on PCMS and PGMA latices are summarized in Table 4.

TABLE 4

| | Covalent Attachment of Rabbit IgG to Latex Particles | | | |
|---|---|---|---|---|
| Type of Shell | Volume of 10% SDS (μL) | Incubation Time (hour) | Incubation Temperature (°C.) | Nitrogen Content (%, Average) |
| PCMS | 100 | 0.5 | 4 | 0.145 |
| | 100 | 0.5* | 4 | 0.685 |
| | 100 | 24 | 4 | 0.245 |
| | 100 | 24 | 37 | 0.470 |
| PGMA | 100 | 0.5 | 4 | 0.00 |
| | 100 | 0.5* | 4 | 0.20 |
| | 100 | 24 | 4 | 0.005 |
| | 100 | 24 | 37 | 0.01 |

*Samples were centrifuged only once, then decanted, and the pellet dried and analyzed. The data indicate incomplete removal of unbound IgG.

The data show that in the presence of added SDS, only PCMS-shell polymer particle of this invention was suitable for immobilization of rabbit IgG.

Example 4

Measurement of Fibrinogen Degradation Products

An automated turbidimetric inhibition immunoassay was performed at 37° C. on the aca ® discrete clinical analyzer (a registered trademark of E. I. du Pont de Nemours & Company). Assay standards were prepared by adding fibrinogen degradation products (FDP) to normal human serum. Fibrinogen degradation products were prepared by degrading 200 mg of purified fibrinogen with 25 CU (casein units) of plasminogen that was activated by 500 U of streptokinase at 37° C. After 1 hour, the reaction was terminated by the addition of soybean trypsin inhibitor to a final concentration of 1 mg/mL. Greater than 95% fibrinogen degrdation was established by comparison of the starting fibrinogen material with the products in the final degradation mixture using a standard SDS-polyacrylamide gel electrophoresis analytical procedure. This FDP solution was then serially diluted to provide the FDP levels calculated from the starting fibrinogen level of 200 mg by assuming substantially complete degradation; see Table 5. The zero level standard was 5% (w/v) human serum albumin in water.

A 20-μL sample of each of the standards, containing the calculated levels of FDP, was automatically added in the filling station of the instrument to 4.98 mL of 0.15M phosphate buffer, pH 7.8, containing 2.5% polyethylene glycol (molecular weight 6,000) and 0.025% sodium dodecyl sulfate. 60-μL of rabbit anti-human fibrinogen antiserum (Cappel Laboratories) were added at breaker-mixer I, followed 3.5 minutes later by addition at breaker-mixer II of 50 μL fibrinogen-PCMS particle reagent prepared in Example 2. The change in turbidity was measured at 340 nm, 39 seconds and 56 seconds, respectively, after particle reagent addition, and the results presented in Table 5 as the extrapolated rate of change in milliabsorbance units over one minute.

TABLE 5

| Fibrinogen Degradation Products Standard Curve | |
|---|---|
| Fibrinogen Degradation Products (μg/mL) | Rate (mAU/min at 340 nm) |
| 0 | 200 |
| 10 | 115 |
| 20 | 83 |
| 40 | 65 |
| 60 | 47 |
| 100 | 30 |

The data show that the turbidimetric rate achieved with fibrinogen-PCMS particle reagent and anti-fibrinogen antibody can be inhibited by adding increasing amounts of fibrinogen degradation products to produce a standard curve. Such a curve obtained with the particle reagent of this invention can be utilized to measure FDP in serum samples over the clinically useful range.

Example 5

Immobilization of Human Serum Albumin (HSA) on Particles Containing Various Levels of Chloromethylstyrene in the Shell (A) Preparation of Polystyrene/Polyvinylnaphthalene/Polychloromethylstyrene Core-Shell Particles An emulsion of polystyrene/polyvinylnaphthalene core polymer particles was prepared as in Example 1Aii. Fifty-two mL of the latex was used to prepare a core-shell latex in the same manner as in Example 1Aiii with chloromethylstyrene monomer. This core-shell polymer had substantially pure polychloromethylstyrene shell.

(B) Preparation of Polystyrene/Polyvinylnaphthalene/Poly(chloromethylstyrene-Co-vinylnaphthalene) Core-Shell Particles The procedure of Example 5A was repeated except for using a mixture of 10 μL of chloromethylstyrene and 90 mg of 2-vinylnaphthalene (VN) as shell monomers to provide a particle shell containing approximately 10% chloromethylstyrene and 90% VN.

(C) Immobilization of HSA 1 mL of latex from each of Examples 5A and 5B, in separate but identical procedures, was first mixed with 50 μL of 10% sodium dodecyl sulfate solution and 4 mL of a 15 mM phosphate buffer, pH 7.5. This suspension was then added to a solution of 10 mg of HSA (Sigma Chemical Co.; crystallized, lyophilized, substantially globulin-free, an amount which is in excess of any available chloromethyl groups) in 15 mM phosphate buffer, pH 7.5. The pH of the mixture was adjusted to 7.8 using 0.1M sodium hydroxide, and incubated for the times and temperatures indicated in Table 6.

After the specified incubation time, each latex was centrifuged at 20,000 RPM in a Sorvall ® model RC-5B centrifuge. The supernatant was decanted from the pellet of particles, and the pellet resuspended in a 0.1% solution of GAFAC ® RE610 in 15 mM phosphate buffer, pH 7.5, by sonication for 3 minutes with a Heat Systems Ultrasonics model 225R sonicator. The suspension was centrifuged a third time, and the pellet resuspended as above. The immobilized protein was measured by hydrolyzing 1% solids latex samples for 20 minutes at 150° C. with 6N hydrochloric acid and determining the amino acid content of the hydrolysate by the o-diphthalaldehyde method (see Methods in Enzymology, Vol. 91, p. 110). The results in Table 6 show that particle shell compositions containing either 10% or 100% chloromethylstyrene can covalently bind protein to approximately the same extent. Multiple washing steps with GAFAC ® RE610 have been shown previously in Example 1 to remove adsorbed protein from particle reagents. To achieve similar protein levels in particle reagents at different incubation temperatures requires different incubation periods.

TABLE 6
Covalent Attachment of HSA to Latex Particles

| Type of Shell | Volume of 10% SDS (μL) | Incubation Time (hour) | Incubation Temperature (°C.) | HSA Bound to Latex (mg/mL) |
| --- | --- | --- | --- | --- |
| 100% PCMS | 50 | 18 | 37 | 0.49 |
|  | 50 | 168 | 4 | 0.48 |
| 10/90% CMS/VN | 50 | 18 | 37 | 0.45 |
|  | 50 | 168 | 4 | 0.42 |

Example 6

Preparation of Particle Reagent for Immunoassays for C-Reactive Protein (A) Polystyrene/Polyvinylnaphthalene Core Polymerization A latex of polyvinylnaphthalene was prepared in a 250 mL round-bottomed flask equipped with a magnetic stirrer and a reflux condenser. A 24-mL quantity of the polystyrene seed emulsion, prepared as in Example 1Ai, was added to 1.75 mL of water and then heated to 95° C. This mixture was added to 20 g of 2-vinylnaphthalene (purified by sublimation and chromatography on basic alumina in a dichloromethane solution), 600 mg of sodium bicarbonate and 180 mg of potassium persulfate. As soon as the 2-vinylnaphthalene had melted, 10 mL of 10% (w/v) sodium dodecyl sulfate solution was added to the mixture at a rate of 0.6 mL/min. One hour after the beginning of the SDS feed, the polymerization was complete. The optical density of the latex polymer measured at 340 nm was 1.128 after diluting 1:100 in water. The number average particle size was determined to be 39.4 nm by electron microscopy. The conversion of monomer to polymer was found to be 99.4% by gas chromatographic determination.

(B) Shell Polymerizations

Four different polymer particles were prepared containing different proportions of monomers in the shell as shown in Table 7. Each preparation began with 50 mL of latex from Example 6A and 1 g of a mixture of chloromethylstyrene and 2-vinylnaphthalene in the appropriate ratio to produce 10, 30, 70, and 100 percent (w/w) chloromethylstyrene/2-vinylnaphthalene shells (lots 6.1, 6.2, 6.3, and 6.4, respectively, the latex from Example 6A having been designated as 6.0). For each preparation, 50 mg of potassium persulfate was used in one-hour polymerizations at 95°–100° C. The monomer conversions and optical densities at 340 nm of a 1:100 dilution in water of the polymer particle latices are also shown in Table 7; the solids content was 14%

TABLE 7
Properties of Core-Shell Particles with Varying Ratio Chloromethylstyrene/Vinylnaphthalene Shells

| Preparation | 2-Vinyl naphthalene (g) | Chloromethylstyrene (mL) | 2-VN conversion (%) | CMS conversion (%) | Optical Density @ 340 nm (1:100) |
| --- | --- | --- | --- | --- | --- |
| 6.0 | 0 | 0 | — | — | 1.128 |
| 6.1 | 0.90 | 0.10 | 99.93 | >97 | 1.734 |
| 6.2 | 0.70 | 0.30 | 99.5 | >97 | 1.695 |
| 6.3 | 0.30 | 0.70 | 99.90 | >97 | 1.640 |
| 6.4 | 0 | 1.0 | — | >96 | 1.648 |

(C) Preparation of Anti-C-Reactive Protein Antibody Particle Reagent

Each of the polymer particle preparations 6.0–6.4 was used to prepare anti-C-reactive protein antibody particle reagents for use in direct immunoassays of CRP.

Purified anti-CRP antibody (IgG) was prepared from immune rabbit serum by precipitation with ammonium sulfate adjusted to a final concentration of 40% (w/v). The precipitate was collected by centrifugation (3000×g; 20 minutes), dissolved in distilled water, precipitated and centrifuged a second time. The precipitate was dissolved in distilled water and dialyzed at 4° C. overnight against 3 changes of 15 mM sodium phosphate buffer, pH 7.5. The level of the final IgG solution was calculated from 280 nm absorbance and adjusted to 1 mg/mL.

A 0.054-mL quantity of each polymer particle preparation was added to 2.05 mL of the 1 mg/mL IgG solution in separate 10 mL Sorvall ® centrifuge tubes. A 2.9-mL quantity of 15 mM phosphate buffer, pH 7.5, was added to each tube and the mixture incubated for 45 minutes at 37° C. (Final IgG levels were 0.41 mg/mL in a buffer with 0.15% particle latex solids.) Preparation 6.0 (latex from Example 6A), without an outer shell, was treated in the same manner except that 0.069 mL of a 10.8% solids suspension was combined with 2.05 mL of 1 mg/mL antibody (IgG) solution in 2.88 mL buffer. (The final IgG level was 0.41 mg/mL in a buffer with 0.19% particle latex solids.)

The particles were centrifuged from suspension at 48,000×g for 90 minutes at 4° C. in a Sorvall ® RC5B refrigerated centrifuge. The supernatant was decanted and the particle pellet resuspended in a wash solution of 50 mM glycine, pH 7.5, in volume equal to the supernatant. This wash step was repeated three times before a final resuspension in 200 mM glycine, pH 7.5, was performed with one third the supernatant volume. This produced a 0.45% solids suspension of anti-CRP particle reagent. As expected, no particle reagent was obtained from preparation 6.0.

(D) Immunoassay for CRP

Each of the anti-CRP antibody particle reagent preparations from Example 6C was used to perform immunoassays for CRP in sodium phosphate buffer pH 7.9, with 2% (w/v) PEG 8000. The assays were performed by mixing 25 μL of anti-CRP particle reagent (from preparations 6.1–6.4 and the control, 6.0) with 996 μL of phosphate buffer having different molarities, ranging from 0.025 to 0.150M, as shown below in Table 8. After the solution had warmed to 37° C., 4 μL of normal human serum containing either 0 or 15 mg/dL CRP was added with mixing and the 340 nm absorbance of the reaction mixture was monitored with a Cary 219 (Varian Instruments) spectrophotometer for two minutes.

The term separation is defined as the difference in absorbance between the 0 and 15 mg/dL CRP level calibrators after a standard reaction period and is represented by the symbol Δ. The data presented in Table 8 as milliabsorbance units show that separation for each shell composition is different at different phosphate buffer molarities. The maximum separation in the CRP assays performed was achieved with a 10% CMS/90% VN shell composition.

TABLE 8

CRP Immunoassay Performance as a Function of Shell Composition

| Phosphate (M) | Particle Reagent (% CMS in Shell) | | | | | | | | | | | | | | |
|---|---|---|---|---|---|---|---|---|---|---|---|---|---|---|---|
| | 0 | | | 10 | | | 30 | | | 70 | | | 100 | | |
| | CRP | | | CRP | | | CRP | | | CRP | | | CRP | | |
| | 0 (mA) | 15 (mA) | Δ | 0 (mA) | 15 (mA) | Δ | 0 (mA) | 15 (mA) | Δ | 0 (mA) | 15 (mA) | Δ | 0 (mA) | 15 (mA) | Δ |
| 0.025 | aggregated | | | 50 | 840 | 790 | 5 | 290 | 285 | 0 | 100 | 100 | 20 | 150 | 130 |
| 0.050 | aggregated | | | 40 | 720 | 680 | 8 | 220 | 212 | — | ND | — | 5 | 25 | 20 |
| 0.100 | 0 | | | 20 | 300 | 280 | 1 | 100 | 99 | — | ND | — | — | ND | — |
| 0.150 | 0 | | | 10 | 170 | 160 | — | ND | — | 0 | 25 | 25 | 0 | 15 | 15 |

What is claimed is:

1. A particle reagent having high refractive index consisting essentially of:
   (A) a polymer particle having an inner core and an outer shell wherein the inner core is a polymer having a refractive index of not less than 1.54 as measured at the wavelength of the sodium D line and wherein the outer shell is a polymer of
      (1) five to about seventy parts by weight of the outer shell of an ethylenically unsaturated monomer having a haloalkyl functional group capable of reacting with a compound of biological interest, its antigen or its antibody, selected from the group consisting of

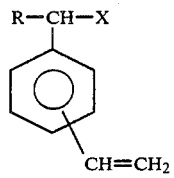

wherein X is Cl or Br and R is H, CH$_3$, or C$_2$H$_5$,
      (2) 95 to about 30 parts by weight of other ethylenically unsaturated monomers selected in amounts not to result in the formation of water soluble polymer particles, and
      (3) not more than 10 parts by weight of the outer shell of the residual monomers of the inner core; said outer shell being formed by polymerization in the presence of said inner core; and wherein said polymer particle has an approximate diameter range of 0.01–1.0 μm, a 5–100% surface coverage by a monomolecular layer of anionic surfactant, and is covalently attached to
   (B) a compound of biological interest, its antigen or its antibody.

2. The particle reagent of claim 1 wherein said outer shell contains at least ten parts by weight of the outer shell of the haloalkyl monomer.

3. The particle reagent of claim 1 wherein said outer shell is not more than ten parts by weight of the polymer particle.

4. The particle reagent of claim 1 wherein the haloalkyl monomer is chloromethylstyrene (X=Cl and R=H).

5. The particle reagent of claim 1 wherein the anionic surfactant covers 40–100% of the polymer particle surface.

6. A method for measuring compounds of biological interest comprising the steps of
   (A) incubating
      (a) a first particle reagent having a high refractive index consisting essentially of:
         (i) a polymer particle having an inner core and an outer shell wherein the inner core is a polymer having a refractive index of not less than 1.54 as measured at the wavelength of the sodium D line and wherein the outer shell is a polymer of
            (1) five to about seventy parts by weight of the outer shell of an ethylenically unsaturated monomer having a haloalkyl functional group capable of reacting with a compound of biological interest, its antigen or its antibody, selected from the group consisting of

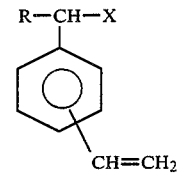

wherein X is Cl or Br and R is H, CH$_3$, or C$_2$H$_5$,
            (2) 95 to about 30 parts by weight of other ethylenically unsaturated monomers selected in amounts not to result in the formation of water soluble polymer particles, and
            (3) not more than 10 parts by weight of the outer shell of the residual monomers of the inner core;
         said outer shell being formed by polymerization in the presence of said inner core; and wherein said polymer particle has an approximate diameter range of 0.01–1.0 μm, a 5–100% surface coverage by a monomolecular layer of anionic surfactant, and is covalently attached to
(ii) a compound of biological interest or its antibody;
(b) a liquid suspected of containing the compound of biological interest or its analog; and
(c) an agglutinating agent; and
(B) photometrically measuring increased particle size resulting from agglutination.

7. The method of claim 6 wherein the agglutinating agent is selected from the group consisting of
(A) a second particle reagent having high refractive index consisting essentially of:
(a) a polymer particle having an inner core and an outer shell wherein the inner core is a polymer having a refractive index of not less than 1.54 as measured at the wavelength of the sodium D line and wherein the outer shell is a polymer of
(1) five to about seventy parts by weight of the outer shell of an ethylenically unsaturated monomer having a haloalkyl functional group capable of reacting with a compound of biological interest, its antigen or its antibody, selected from the group consisting of

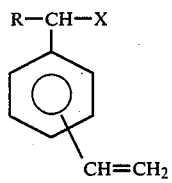

wherein X is Cl or Br and R is H, CH$_3$, or C$_2$H$_5$,
(2) 95 to about 30 parts by weight of other ethylenically unsaturated monomers selected in amounts not to result in the formation of water soluble polymer particles, and
(3) not more than 10 parts by weight of the outer shell of the residual monomers of the inner core;
said outer shell being formed by polymerization in the presence of said inner core; and wherein said polymer particle has an approximate diameter range of 0.01–1.0 μm, a 5–100% surface coverage by a monomolecular layer of anionic surfactant, and is covalently attached to
(b) a compound of biological interest, its antigen or its antibody selected to be immunochemically complementary to the compound of biological interest or its antibody; and
(B) an antibody to the compound of biological interest.

8. The method of claim 6 wherein during the incubation step (A) there is also present an agglutinating accelerator.

9. A method for measuring antibodies comprising the steps of
(A) incubating
(a) a particle reagent having a high refractive index consisting essentially of:
(i) a polymer particle having an inner core and an outer shell wherein the inner core is a polymer having a refractive index of not less than 1.54 as measured at the wavelength of the sodium D line and wherein the outer shell is a polymer of
(1) five to about seventy parts by weight of the outer shell of an ethylenically unsaturated monomer having a haloalkyl functional group capable of reacting with a compound of biological interest, its antigen or its antibody, selected from the group consisting of

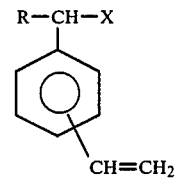

wherein X is Cl or Br and R is H, CH$_3$, or C$_2$H$_5$,
(2) 95 to about 30 parts by weight of other ethylenically unsaturated monomers selected in amounts not to result in the formation of water soluble polymer particles, and
(3) not more than 10 parts by weight of the outer shell of the residual monomers of the inner core;
said outer shell being formed by polymerization in the presence of said inner core; and wherein said polymer particle has an approximate diameter range of 0.01–1.0 μm, a 5–100% surface coverage by a monomolecular layer of anionic surfactant, and is covalently attached to
(ii) an antibody to the antibody or an antigen of the antibody;
(b) a liquid suspected of containing the antibody; and
(c) an agglutinating agent; and
(B) photometrically measuring increased particle size resulting from agglutination.

10. A method for measuring compounds of biological interest comprising the steps of
(A) incubating
(a) a particle reagent having a high refractive index consisting essentially of:
(i) a polymer particle having an inner core and an outer shell wherein the inner core is a polymer having a refractive index of not less than 1.54 as measured at the wavelength of the sodium D line and wherein the outer shell is a polymer of
(1) five to about seventy parts by weight of the outer shell of an ethylenically unsaturated monomer having a haloalkyl functional group capable of reacting with a compound of biological interest, its antigen or its antibody, selected from the group consisting of

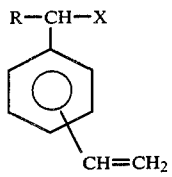

wherein X is Cl or Br and R is H, CH₃, or C₂H₅, (2) 95 to about 30 parts by weight of other ethylenically unsaturated monomers selected in amounts not to result in the formation of water soluble polymer particles, and (3) not more than 10 parts by weight of the outer shell of the residual monomers of the inner core;

said outer shell being formed by polymerization in the presence of said inner core; and wherein said polymer particle has an approximate diameter range of 0.01–1.0 μm, a 5–100% surface coverage by a monomolecular layer of anionic surfactant, and is covalently attached to (ii) the antibody to the compound of biological interest;

(b) a liquid suspected of containing the compound of biological interest or its analog; and (B) photometrically measuring increased particle size resulting from agglutination.

* * * * *